United States Patent [19]

Das et al.

[11] Patent Number: 5,691,356
[45] Date of Patent: Nov. 25, 1997

[54] DISUBSTITUTED HETEROCYCLIC THROMBIN INHIBITORS

[75] Inventors: Jagabandhu Das, Mercerville; Spencer D. Kimball, E. Windsor; Wan Fang Lau, Lawrenceville, all of N.J.

[73] Assignee: Bristol-Myers Squibb Company, Princeton, N.J.

[21] Appl. No.: 708,292

[22] Filed: Sep. 4, 1996

Related U.S. Application Data

[63] Continuation of Ser. No. 215,433, Mar. 21, 1994, abandoned.

[51] Int. Cl.[6] .................. A61K 31/445; A61K 31/40; A61K 31/495; A61K 31/535; A61K 31/54; C07D 401/12; C07D 207/09; C07D 211/28

[52] U.S. Cl. .................. 514/326; 514/183; 514/200; 514/212; 514/231.5; 514/233.8; 514/234.5; 514/235.2; 514/235.5; 514/235.8; 514/236.8; 514/237.2; 514/252; 514/256; 514/258; 514/266; 514/321; 514/422; 514/423; 540/354; 540/480; 540/483; 540/544; 540/553; 540/597; 540/600; 540/603; 544/124; 544/127; 544/128; 544/129; 544/130; 544/133; 544/135; 544/137; 544/139; 544/141; 544/238; 544/242; 544/277; 544/283; 544/336; 546/208; 546/209; 546/210; 546/211; 546/212; 546/214; 548/517; 548/548; 548/572

[58] Field of Search .................. 546/208, 209, 546/210, 211, 212, 214; 540/354, 480, 483, 544, 553, 597, 600, 603; 544/124, 127, 128, 129, 130, 133, 135, 137, 139, 141, 238, 242, 277, 283, 336; 548/548, 517, 572; 514/326, 183, 200, 212, 231.5, 233.8, 234.5, 235.2, 235.5, 235.8, 236.8, 237.2, 252, 256, 258, 266, 321, 319, 422, 423

[56] References Cited

U.S. PATENT DOCUMENTS

| | | | |
|---|---|---|---|
| 4,258,192 | 3/1981 | Okamoto et al. | 546/166 |
| 4,346,078 | 8/1982 | Bajusz et al. | 424/177 |
| 4,904,661 | 2/1990 | Pilgrim et al. | 514/237.5 |
| 5,002,964 | 3/1991 | Loscalzo | 514/423 |
| 5,430,023 | 7/1995 | Gesellchen et al. | 514/18 |
| 5,439,888 | 8/1995 | Shuman et al. | 514/18 |

FOREIGN PATENT DOCUMENTS

WO9311152  6/1993  WIPO.

OTHER PUBLICATIONS

Robert M. Knabb et al, "In Vivo Characterization of a New Synthetic Thrombin Inhibitor," Thrombosis and Hemostasis (1992) 67, 56–59.

Charles V. Jackson et al, "Pharmacological Assessment of the Antithrombotic Activity of the Peptide Thrombin Inhibitor, D–Methyl–Phenylalanyl–Prolyl–Arginal (GYKI–14766), in Canine Model of Coronary Artery Thrombosis," J. Pharm. Exp. Ther. (1992) 261, 546–552.

*Primary Examiner*—C. Warren Ivy
*Assistant Examiner*—Evelyn Huang
*Attorney, Agent, or Firm*—Burton Rodney

[57] ABSTRACT

Disubstituted heterocyclic thrombin inhibitors are provided which have the structure

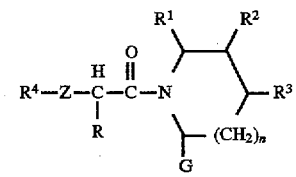

wherein G is

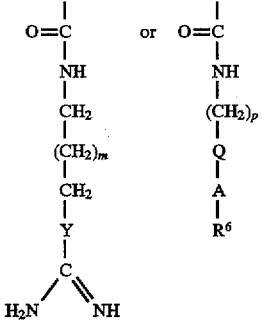

wherein n is 0, 1 or 2 or 3; m is 0, 1, 2 or 3; Y is NH or S; p is 0, 1 or 2, Q is a single bond or

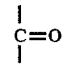

and Z, A, R, $R^1$, $R^2$, $R^3$, $R^4$ and $R^6$ are as defined herein.

11 Claims, No Drawings

DISUBSTITUTED HETEROCYCLIC THROMBIN INHIBITORS

This is a CONTINUATION of application Ser. No. 08/215,433, filed Mar. 21, 1994 abandoned.

FIELD OF THE INVENTION

The present invention relates to disubstituted heterocyclic compounds which are thrombin inhibitors and thus useful in inhibiting formation of thrombi.

DESCRIPTION OF THE INVENTION

The disubstituted heterocyclic thrombin inhibitors of the invention have the structure I

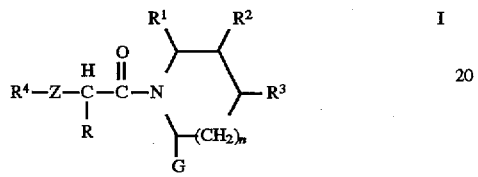

wherein G is an amido moiety which is

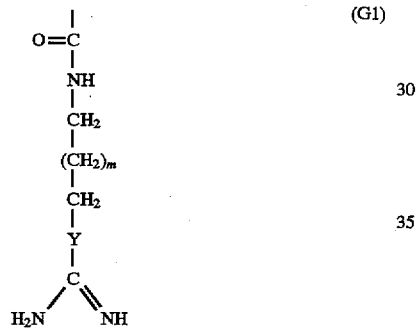

or

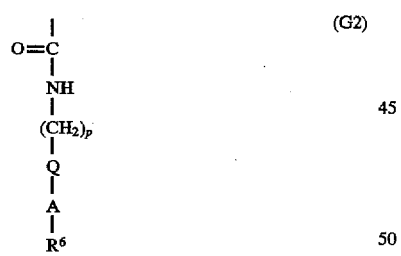

including all stereoisomers thereof; and including all pharmaceutically acceptable salts thereof;

wherein

R is hydrogen, hydroxyalkyl, hydroxyalkyl(alkyl), aminoalkyl, amidoalkyl, lower alkyl, cycloalkyl, aryl, arylalkyl, alkenyl, alkynyl, arylalkoxyalkyl, or an amino acid side chain, either protected or unprotected;

$R^1$ is lower alkyl, cycloalkyl, aryl, or arylalkyl; or $R^1$ and $R^2$ together with the carbons to which they are attached form a cycloalkyl, aryl or heteroaryl ring;

$R^2$ and $R^3$ are independently hydrogen, lower alkyl, cycloalkyl, aryl, arylalkyl, hydroxy, alkoxy, oxo, thioketal, thioalkyl, thioaryl, amino or alkylamino; or $R^2$ and $R^3$ together with the carbons to which they are attached form a cycloalkyl, aryl, or heteroaryl ring;

$R^4$ is hydrogen, lower alkyl, aryl, arylalkyl,

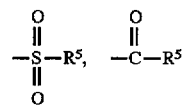

or $-CO_2R^5$ wherein $R^5$ is lower alkyl, aryl, arylalkyl, cycloheteroalkyl, heteroaryl, quinolinyl or tetrahydroquinolinyl;

n is 0, 1 or 2;

m is 0, 1, 2 or 3;

Z is $NR^7$ or O (where $R^7$ is H, lower alkyl, aryl or arylalkyl);

Y is NH or S;

p is 0, 1 or 2;

Q is a single bond or

A is aryl or cycloalkyl, or an azacycloalkyl ring A' of 4 to 8 carbons in the ring or an azaheteroalkyl ring $A'R^6$ of 4 to 8 carbons in the ring, A'

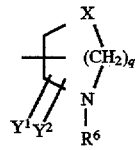

where X is $CH_2$, O, S or NH;

q is 0, 1, 2, 3 or 4 if X is $CH_2$;

q is 2, 3 or 4 if X is O, S or NH;

$Y^1$ and $Y^2$ are independently H, lower alkyl, halo or keto; and $R^6$ is guanidine, amidine or aminomethyl;

provided that where A is aryl or cycloalkyl, $R^6$ is guanidine, amidine or aminomethyl;

where A is azacycloalkyl or azaheteroalkyl, $R^6$ is amidine;

provided that where X is a hetero atom (that is, A is azaheteroalkyl), then there must be at least a 2-carbon chain between X and any N atom in the ring A' or outside ring A'.

Examples of the A' ring (azacycloalkyl, or azaheteroalkyl) which may be employed herein include

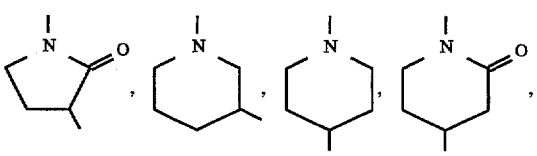

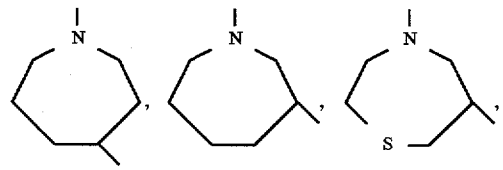

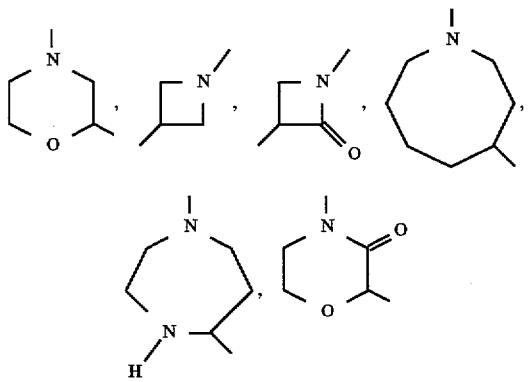

and the like.

The term "lower alkyl" or "alkyl" as employed herein by itself or as part of another group includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents (for example, to form $CF_3$ or $CF_3CH_2$) and/or 1 or 2 of the following substituents: an aryl substituent (for example, to form benzyl or phenethyl), an alkyl-aryl substituent, a haloaryl substituent, a cyclo-alkyl substituent, an alkylcycloalkyl substituent, an alkenyl substituent, an alkynyl substituent, hydroxy or a carboxy substituent. It will be appreciated that the same "alkyl" group may be substituted with one or more of any of the above substituents.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy groups.

The term "aryl" or "Ar" as employed herein by itself or as part of another group refers to monocyclic or bicyclic aromatic groups containing from 6 to 10 carbons in the ring portion, such as phenyl, or naphthyl. Aryl (or Ar), phenyl or naphthyl may include substituted aryl, substituted phenyl or substituted naphthyl, which may include 1 or 2 substituents on either the Ar, phenyl or naphthyl such as lower alkyl, cyano, amino, alkylamino, dialkylamino, nitro, carboxy, carboalkoxy, trifluoromethyl, halogen (Cl , Br, I or F), lower alkoxy, arylalkoxy, hydroxy, alkylthio, alkylsulfinyl, alkylsulfonyl, arylthio, arylsulfinyl and/or arylsulfonyl.

The term "aralkyl", "aryl-alkyl" or "aryl-lower alkyl" as used herein by itself or as part of another group refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein by itself or as part of another group refers to chlorine, bromine, fluorine or iodine.

The term "lower alkenyl" or "alkenyl" as employed herein by itself or as part of another group includes a carbon chain of up to 16 carbons, preferably 3 to 10 carbons, containing one double bond which will be separated from "N" by at least one saturated carbon moiety such as —$(CH_2)_q$— where q can be 1 to 14, such as 2-propenyl, 2-butenyl, 3-butenyl, 2-pentenyl, 4-pentenyl and the like, and may include a halogen substituent such as I, Cl, or F.

The term "lower alkynyl" or "alkynyl" as employed herein by itself or as part of another group includes a carbon chain of up to 16 carbons, preferably 3 to 10 carbons, containing one triple bond which will be separated from "N" by at least one saturated carbon moiety such as —$(CH2)_{q'}$— where q' can be 1 to 14, such as 2-propynyl, 2-butynyl, 3-butynyl and the like.

The term "heteroaryl" or heteroaromatic by itself or as part of another group refers to a 5- or 6-membered aromatic ring which includes 1 or 2 hetero atoms such as nitrogen, oxygen or sulfur, such as

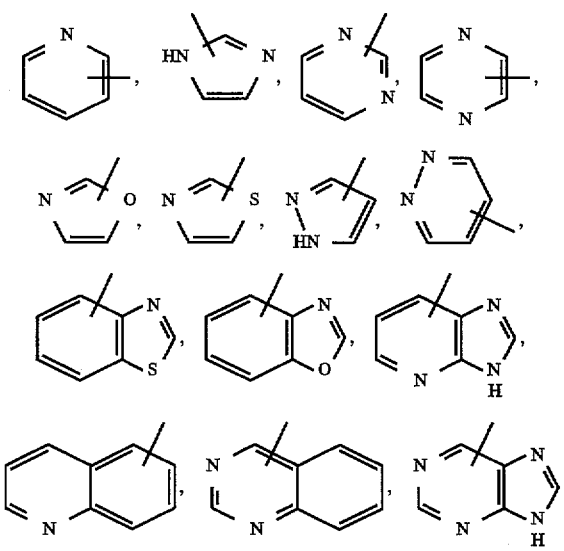

and the like. The heteroaryl rings may optionally be fused to aryl rings defined previously. The heteroaryl rings may optionally include 1 or 2 substituents such as halogen (Cl , Br, F or $CF_3$), lower alkyl, lower alkoxy, carboxy, amino, lower alkylamino and/or dilower alkylamino.

The term "amino acid side chain" refers to any side chain of the known natural or synthetic alpha-amino acids such as arginine, histidine, alanine, glycine, lysine, glutamine, leucine, valine, serine, homoserine, allothreonine, isoleucine, phenylalanine 2-naphthylalanine, p-chlorophenylalanine, and the like.

Thus the amino acid side chain can include the side chain H of glycine, the side chain

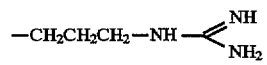

of arginine the side chain

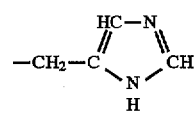

of histidine, the side chain —$CH_2CH_2CH_2CH_2$—$NH_2$ of lysine, the side chain $$-CH_2-\overset{\overset{O}{\|}}{C}-NH_2$$

of asparagine, the side chain —$CH_2$—OH of serine, the side chain $$-CH\overset{OH}{\underset{CH_3}{\diagup}}$$

of threonine or allothreonine, the side chain —$CH_2CH_2OH$ of homoserine, the side chain $$-CH_2CH_2\overset{\overset{O}{\|}}{C}-NH_2$$

of glutamine, the side chain $$-CH_2-CH\overset{CH_3}{\underset{CH_3}{\diagup}}$$

of leucine, the side chain —$CH_3$ of alanine, the side chain —$CH_2$—$C_6H_5$ of phenylalanine, the side chain $$-CH\overset{CH_3}{\underset{CH_2CH_3}{\diagup}}$$

of isoleucine, the side chain $$-CH\overset{CH_3}{\underset{CH_3}{\diagup}}$$

of valine, the side chain $$-CH_2-\text{[naphthyl]}$$

of 2-naphthylalanine, or the side chain $$-CH_2-\text{[phenyl]}-Cl$$

of p-chlorophenylalanine.

Preferred are compounds of formula I wherein G is $$\begin{array}{c} | \\ O=C \\ | \\ NH \\ | \\ CH_2 \\ | \\ Q \\ | \\ A \\ | \\ R^6 \end{array}$$

wherein R is H, p is 1, Z is NH, Q is a single bond, A is an azacycloalkyl ring $$\text{[azacycloalkyl ring with }(CH_2)_q\text{]}$$

where q is 0 or 1; and $R^1$ is arylalkyl such as benzyl, or alkyl;

$R^2$ and $R^3$ are independently H and/or alkyl;

$R^4$ is benzyloxycarbonyl, alkylsulfonyl, such as methylsulfonyl or alkyl such as ethyl;

$R^6$ is amidino;

n is 0 or 1.

Another preferred embodiment of the heterocyclic thrombin inhibitors of the invention of formula I wherein G is $$\begin{array}{c} | \\ O=C \\ | \\ NH \\ | \\ CH_2 \\ | \\ (CH_2)_m \\ | \\ CH_2 \\ | \\ A \\ | \\ C \\ H_2N\diagup \quad \diagdown NH \end{array}$$

where $R^4$ is benzyloxycarbonyl, or alkylsulfonyl such as methyl sulfonyl, Z is NH, R is H, $R^1$ is arylalkyl such as benzyl, $R^2$ and $R^3$ are independently H and/or alkyl, m is 2 and A is NH.

The compounds of formula I of the invention wherein G is (G1)

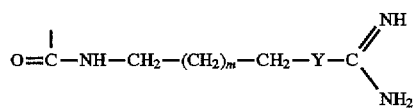

and Y is NH may be prepared according to the following Reaction Sequence I.

Reaction Sequence I

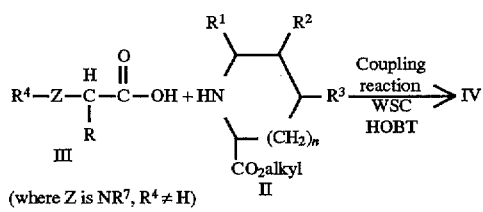

(where Z is $NR^7$, $R^4 \neq H$)

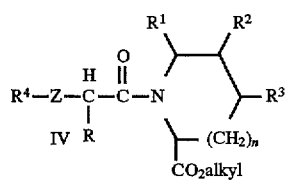

1) Hydrolysis (Base)
2) Coupling reaction $H_2N-CH_2-(CH_2)_m-CH_2-N(H)-P^1$ ($P^1$ = carbobenzyloxy, t-butoxycarbonyl, phthalimido)

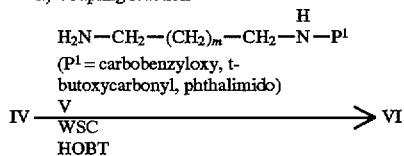

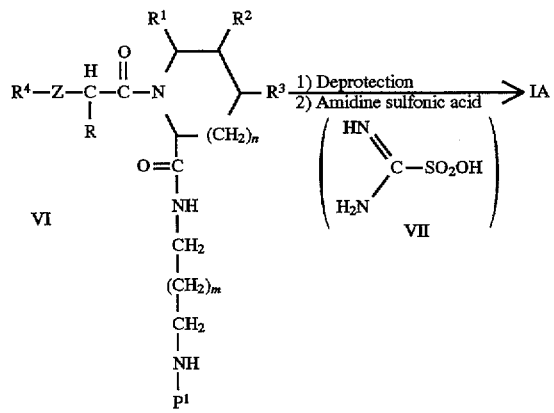

-continued
Reaction Sequence I

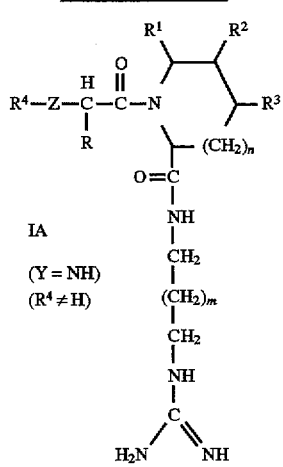

The compounds of formula I of the invention wherein G is

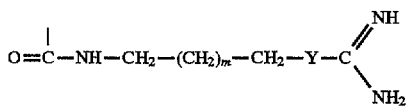

and Y is NH may also be prepared according to the following Reaction Sequence II Reaction Sequence II

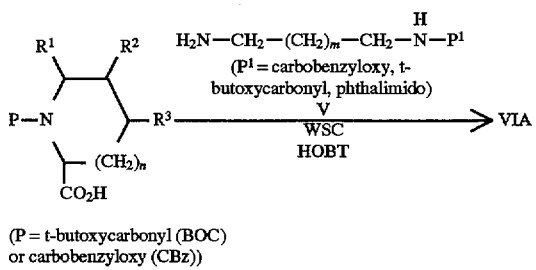

(P = t-butoxycarbonyl (BOC) or carbobenzyloxy (CBz))

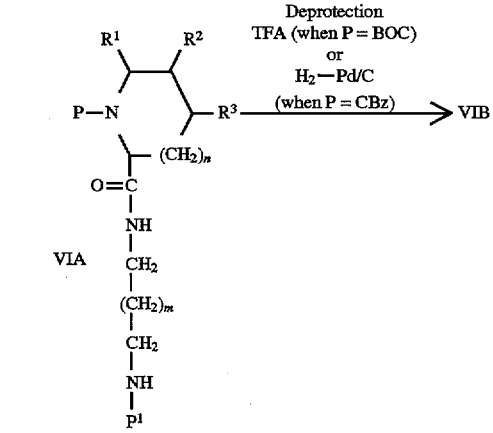

-continued
Reaction Sequence II

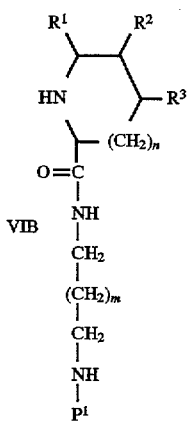

VIB

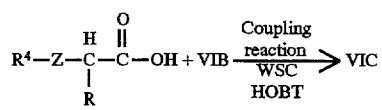

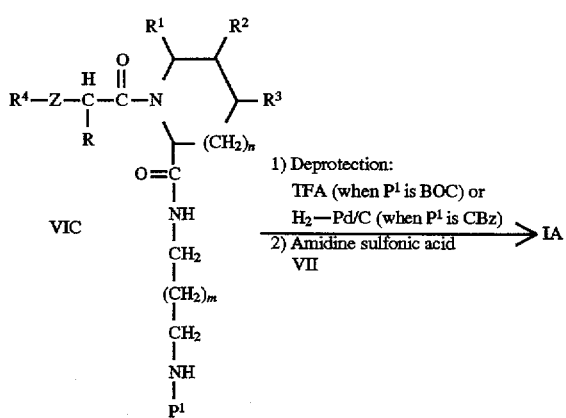

VIC

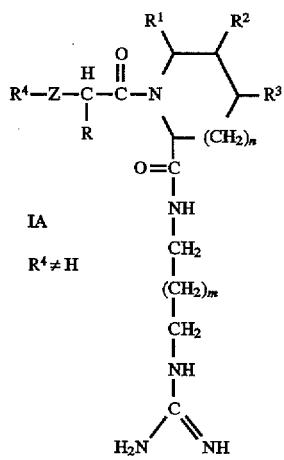

IA
$R^4 \neq H$

As seen in the above Reaction Sequence I, compounds of formula I wherein the G chain is (G1) and Y is —NH—, are prepared as follows. The ester II is made to undergo a carbodiimide coupling reaction with protected amino acid III (where $R^4$ is other than H) in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the ester IV. Ester IV is hydrolyzed by treatment with alkali metal base such as NaOH or LiOH in the presence of an alcohol solvent such as methanol or ethanol. The reaction mixture is acidified with HCl, $KHSO_4$ or $H_2SO_4$, to form the corresponding acid of IV. The acid is subjected to a carbodiimide coupling reaction wherein the acid is treated with protected amine V in the presence of WSC or DCC, and HOBT, and NMM, in the presence of an inert organic solvent such as dimethylformamide, THF or N-methylpyrrolidone, to form amide VI. The amide VI is then dissolved in an alcohol solvent such as ethanol or methanol, to which HCl has been added and the mixture is hydrogenated over Pd—C or $Pd(OH)_2$—C in the case where $P^1$ is carbobenzyloxy. The crude material is separated by conventional procedures and the desired isomers are treated with amidine sulfonic acid VII in the presence of an alcohol solvent such as ethanol to form the compound of the invention IA.

The compounds of formula I of the invention wherein the G chain is (G1), Y is NH and $R^4$ is H, may be prepared starting with compound III where $R^4$ is carbobenzyloxy (CBz) and Z is $NR^7$ and following Reaction Sequence I to form compound of the invention IB

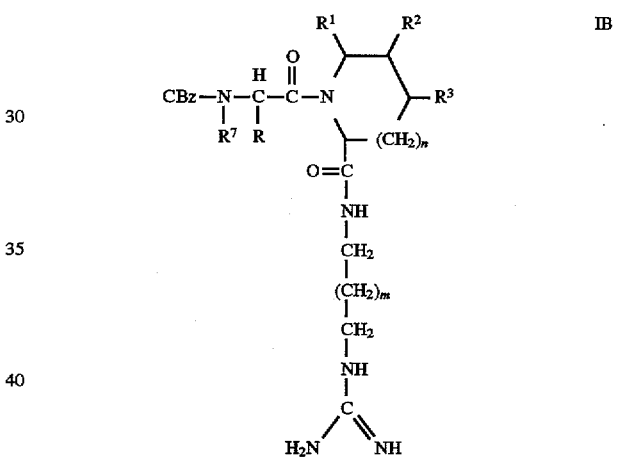

and hydrogenating IB by reaction with $H_2$ in the presence of a hydrogenation catalyst such as Pd/C to form compound of the invention IC, that is IB where CBz is replaced with H.

As seen in the above Reaction Sequence II, compounds of formula I wherein the G chain is (G1) and Y is —NH—, are also prepared as follows. The protected acid IIA is made to undergo a carbodiimide coupling reaction with protected amino acid V in the presence of ethyl 3-(3-dimethylamino) propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide VIA. Amide VIA is deprotected by treatment with trifluoroacetic acid (TFA) when P is t-butoxycarbonyl (BOC) or $H_2$—Pd/C when P is carbobenzyloxy (CBz), with or without the presence of dry inert organic solvent such as dichloromethane, chloroform or THF, at temperatures within the range of from about −15° to about 20° C. to form amide VIB. The amide VIB is then subjected to a carbodiimide coupling reaction wherein VIB is treated with protected acid III in the presence of WSC or DCC, and HOBT, and NMM, in the presence of an inert organic solvent such as dimethylformamide, THF or N-methylpyrrolidone, to form amide VIC. The amide VIC is then dissolved in an alcohol solvent such as ethanol or methanol, to which HCl has been added and the mixture is hydrogenated over Pd—C or Pd(OH)$_2$—C in the case where P$^1$ is CBz or treated with trifluoroacetic acid when P$^1$ is BOC. The crude material is separated by conventional procedures and the desired isomers are treated with amidine sulfonic acid VII in the presence of an alcohol solvent such as ethanol to form compound of the invention IA.

In Reaction Sequence II, the compounds of formula I of the invention where the chain G is (G1), Y is NH and R$^4$ is H may be prepared starting with compound III where R$^4$ is carbobenzyloxy (CBz) and Z is NR$^7$ and following Reaction Sequence II to form

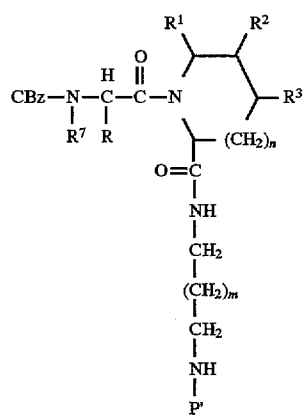

and deprotecting VIC' and then reacting with amidine sulfonic acid to form compound of the invention IB and hydrogenating IB by reaction with H$_2$ in the presence of a hydrogenation catalyst such as Pd/C to form a compound of the invention IC, that is IB where CBz is replaced by H.

The compounds of formula I of the invention wherein G is

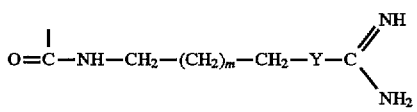

and Y is S may be prepared according to the following Reaction Sequence III.

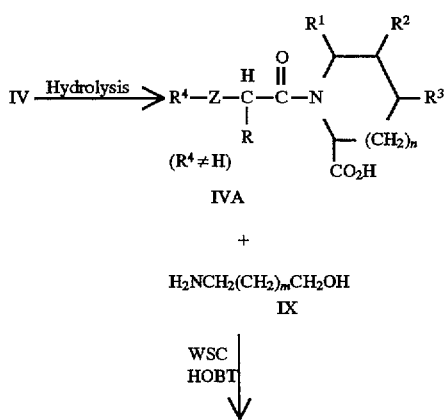

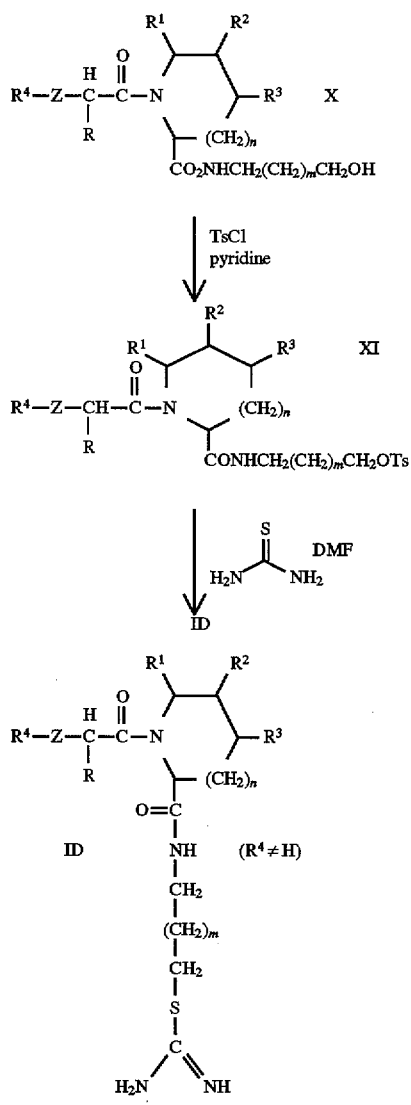

Referring to the above Reaction Sequence III, compounds of formula I wherein the G chain is (G1) and Y=S can be prepared as follows. The ester IV is hydrolyzed as described above with respect to Reaction Scheme I to form acid IVA. The acid IVA is subjected to a carbodiimide coupling reaction wherein IVA is treated with an aminoalcohol IX in the presence of WSC or DCC, HOBT, and NMM, in the presence of an inert organic solvent such as dimethylformamide, THF or N-methylpyrrolidone, to form amide alcohol X. The amide alcohol X is reacted with p-toluenesulfonyl chloride (TsCl) in pyridine, or in a solvent such as methylene chloride or chloroform, with N,N-dimethylaminopyridine to provide toluenesulfonate XI. The compounds of the invention ID (Y=S) are prepared by treating XI with thiourea in a solvent such as DMF or DMSO at temperatures within the range of from about 25° C. to about 100° C.

The compounds of formula I of the invention where the G chain is (G1), Y is S and R$^4$ is H, may be prepared starting with compound IVA where R$^4$ is carbobenzyloxy (CBz) and Z is NR$^7$ and following Reaction Sequence III to form compound of the invention IE

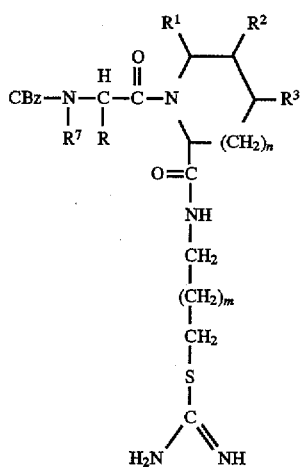

and hydrogenating IE by reaction with $H_2$ in the presence of a hydrogenation catalyst such as Pd/C to form compound of the invention IF, that is IE where CBz is replaced with H.

The compounds of formula I of the invention wherein G is (G2), that is

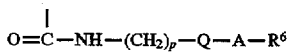

wherein A is azacycloalkyl or azaheteroalkyl, and $R^6$ is amidine, may be prepared according to the following Reaction Sequence IV:

Reaction Sequence IV

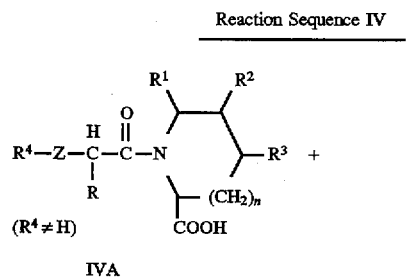

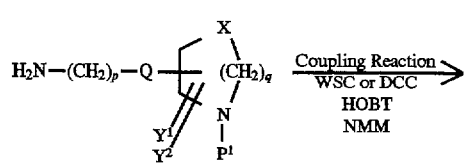

(where $P^1$ is a protecting group such as BOC or CBz)

-continued
Reaction Sequence IV

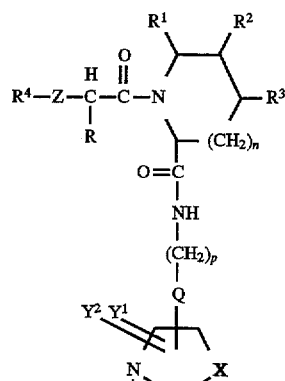

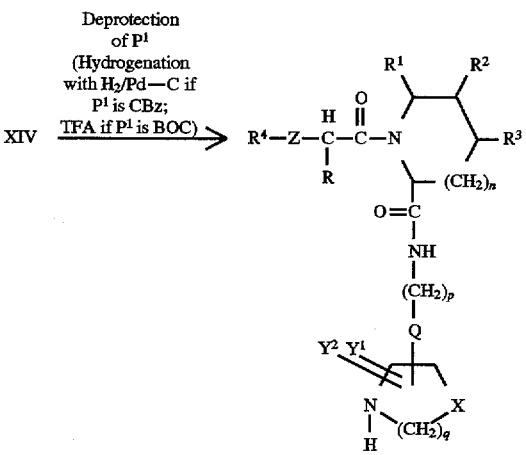

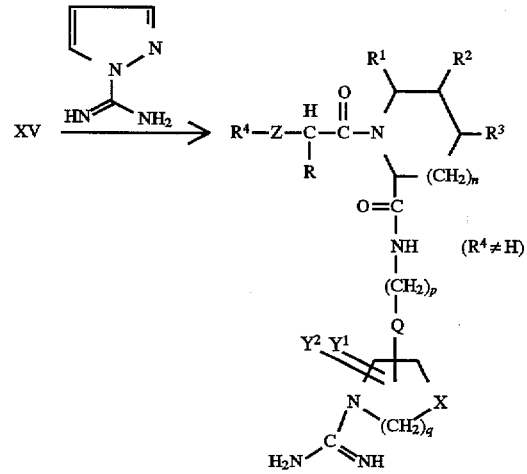

As seen in the above Reaction Sequence IV, compounds of formula I wherein G is (G2)

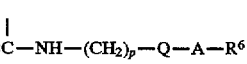

and A is azacycloalkyl or azaheteroalkyl, are prepared as follows. The protected acid IVA is made to undergo a carbodiimide coupling reaction with amine XIII in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide XIV. Amide XIV is deprotected by treatment with, for example, $H_2$/Pd—C, if $P^1$ is CBz, to form amine XV. Amine XV is treated with H-pyrazole-1-carboxamidine in the presence of solvent, such as dimethylformamide (DMF) and amine base such as diisopropylethylamine to form compound of the invention IG.

The compounds of formula I of the invention where $R^4$ is H and A is azacycloalkyl or azaheteroalkyl may be prepared starting with compound IVA where $R^4$ is carbobenzyloxy (CBz) and Z is $NR^7$ and following Reaction Sequence IV to form IG where $R^4$ is CBz and hydrogenating IG by reaction with $H_2$ in the presence of a hydrogenation catalyst such as Pd/C to form IH, that is IG where CBz is replaced with H.

The starting materials of formula XIII are known in the art or may be prepared by those skilled in the art employing conventional techniques.

The compounds of formulae I and IA of the invention where G is (G2)

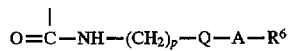

where A is aryl or cycloalkyl and $R^6$ is amidine or guanidine may be prepared according to the following Reaction Sequence V:

Reaction Sequence V

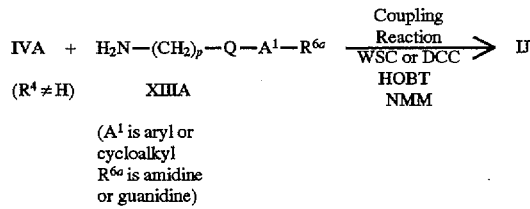

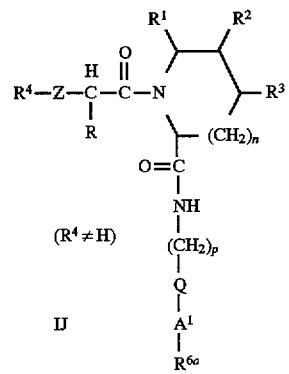

As seen in Reaction Sequence V, compounds of formulae I and IA where G is (G2)

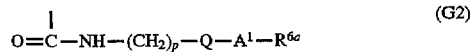

are prepared as follows. The protected acid IVA is subjected to a carbodiimide coupling reaction wherein IVA is treated with protected amine XIIIA in the presence of WSC or DCC, and HOBT, and NMM, in the presence of an inert organic solvent such as dimethylformamide, THF or N-methylpyrrolidone, to form compound of the invention IJ.

The compounds of Formula I of the invention where the chain G is (G2) and $R^4$ is H may be prepared starting with compound IVA where $R^4$ is carbobenzyloxy (CBz) and Z is $NR^7$ and following Reaction Sequence V to form compound of the invention IJ where $R^4$ is CBz, and hydrogenating IJ by reaction with $H_2$ in the presence of a hydrogenation catalyst such as Pd/C to form IK, that is IJ where CBz is replaced with H.

The starting compound XIIIA is known in the art or may be prepared employing conventional procedures.

The compounds of formulae I and IA of the invention wherein G is

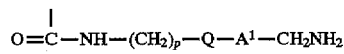

where A is aryl or cycloalkyl (that is $A^1$) and $R^6$ is aminomethyl may be prepared according to the following Reaction Sequence VI:

Reaction Sequence VI

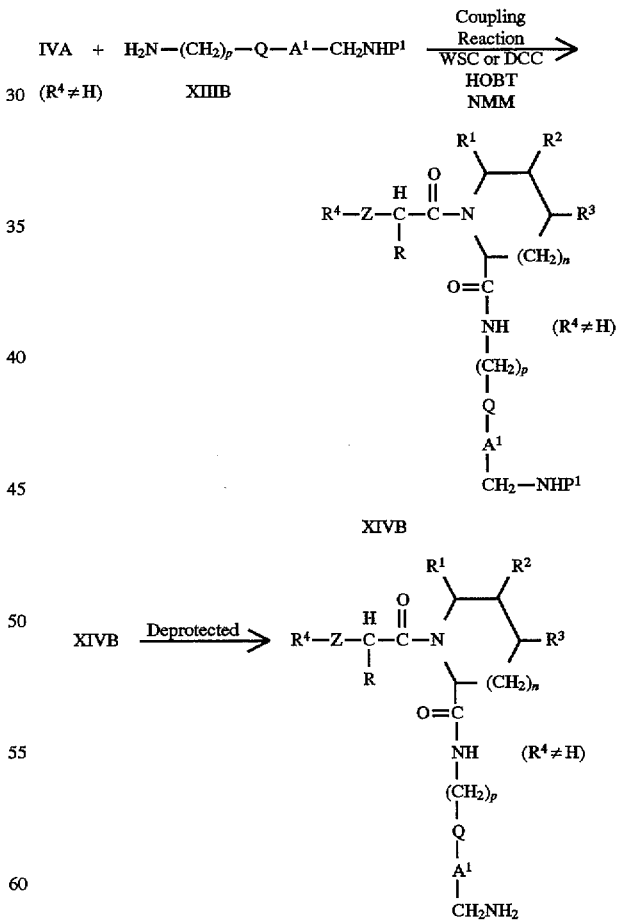

As seen in the above Reaction Sequence VI, compounds of formula I of the invention wherein G is G(2) and $R^6$ is $CH_2NH_2$

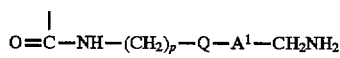

are prepared as follows. The protected acid IVA is made to undergo a carbodiimide coupling reaction with protected amino acid XIIIB in the presence of ethyl 3-(3-dimethylamino)propyl carbodiimide hydrochloride (WSC) or dicyclohexylcarbodiimide (DCC), and 1-hydroxybenzotriazole monohydrate (HOBT), and N-methylmorpholine (NMM), and in the presence of an inert organic solvent such as dimethylformamide (DMF), THF or N-methylpyrrolidone, to form the amide XIVB. Amide XIVB is deprotected by treatment with trifluoroacetic acid (TFA) when P is t-butoxycarbonyl (BOC) or $H_2$—Pd/C when P is carbobenzyloxy (CBz), with or without the presence of dry inert organic solvent such as dichloromethane, chloroform or THF, at temperatures within the range of from about −15° to about 20° C. to form compounds of the invention IL.

The starting compounds XIIIB are known in the art or may be prepared employing conventional procedures.

The compounds of Formula I of the invention where $R^4$ is H may be prepared starting with IVA where $R^4$ is CBz and Z is $NR^7$ and following Reaction Sequence VI to form IL where $R^4$ is CBz and hydrogenating IL by reaction with $H_2$ in the presence of a hydrogenation catalyst such as Pd/C to form IM, that is IL where $R^4$ is H.

The starting acid IVA may be prepared from ester IV by hydrolyzing ester IV by treating with a base such as NaOH, KOH or LiOH and then neutralizing the resulting alkali metal salt with strong acid such as HCl or oxalic acid.

The compounds of formula I of the invention can be obtained as pharmaceutically acceptable acid addition salts by reacting a free base with an acid, such as hydrochloric, hydrobromic, hydroiodic, nitric, sulfuric, phosphoric, acetic, citric, maleic, succinic, lactic, tartaric, gluconic, benzoic, methanesulfonic, ethanesulfonic, benzenesulfonic, p-toluenesulfonic acid or the like.

The compounds of the present invention are serine protease inhibitors, and in particular may inhibit thrombin, Factor Xa, and/or trypsin. The compounds of the present invention are useful for the treatment or prophylaxis of those processes which involve the production and/or action of thrombin. This includes a number of thrombotic and pro-thrombotic states in which the coagulation cascade is activated which include, but are not limited to, deep vein thrombosis (DVT), disseminated intravascular coagulopathy (DIC), Kasabach-Merritt syndrome, pulmonary embolism, myocardial infarction, stroke, thromboembolic complications of surgery (such as hip replacement and endarterectomy) and peripheral arterial occlusion. In addition to its effects on the coagulation process, thrombin has been shown to activate a large number of cells (such as neutrophils, fibroblasts, endothelial cells, smooth muscle cells). Therefore, the compounds of the present invention may also be useful for the treatment or prophylaxis of adult respiratory distress syndrome, septic shock, septicemia, inflammatory responses which include, but are not limited to, edema, acute or chronic atherosclerosis, and reperfusion damage.

The compounds of the invention may also be useful in treating neoplasia/metastasis (in particular those which utilize fibrin) and neurodegenerative diseases such as Alzheimer's disease and Parkinson's disease. In addition, the compounds of the present invention may be useful to prevent restenosis following arterial injury induced by endogenous (rupture of an atherosclerotic plaque) or exogenous (invasive cardiological procedure) events.

The compounds of the present invention may also be used as an anticoagulant in extracorpeal blood circuits, such as those necessary in dialysis and surgery (such as coronary artery bypass surgery).

The compounds of the present invention may also be used in combination with thrombolytic agents, such as tissue plasminogen activator (natural or recombinant), streptokinse, urokinase, prourokinase, anisolated streptokinase plasminogen activator complex (ASPAC), animal salivary gland plasminogen activators, and the like. The compounds of the present invention may act in a synergistic fashion to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention may also be used in combination with other antithrombotic or anticoagulant drugs such as thromboxane receptor antagonists, prostacyclin mimetics, phosphodiesterase inhibitors, fibrinogen antagonists, and the like.

Compounds of the present invention that inhibit trypsin may also be useful for the treatment of pancreatitis.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc., as called for by accepted pharmaceutical practice.

The following Examples represent preferred embodiments of the present invention. All temperatures are expressed in degrees Centigrade.

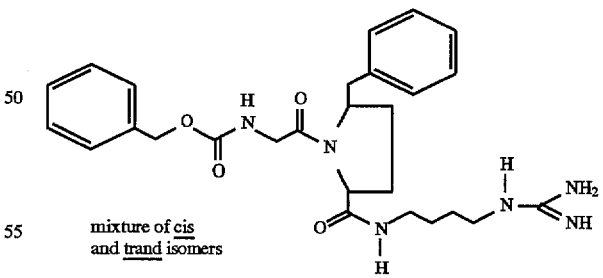

mixture of cis and trand isomers

A. Ethyl-N-(diphenylmethylene)glycinate

A suspension of glycine ethylester, monohydrochloride (13.96 g, 100 mmol) and benzophenone imine (18.1 g, 100 mmol) in distilled dichloromethane (600 mL) was stirred at room temperature (RT) for 24 hours (h.). The mixture was diluted with water (250 mL) and the dichloromethane extract was separated, dried ($MgSO_4$), filtered and concentrated under reduced pressure and in vacuo to obtain ethyl- N-(diphenylmethylene)-glycinate as a white solid (25.3 g, 95%). Ref.: M. J. O'Donnell, R. L. Polt *J. Org. Chem.* 47, 2663, 1982.

B. 4-Phenyl-but-1-ene-3-one

A 1M solution of vinylmagnesium bromide in THF (80 mL, 80 mmol) was added dropwise to a stirred solution of N-methoxy-N-methylphenylacetamide (12.8 g, 71.5 mmol) in distilled tetrahydrofuran (THF) (200 mL), cooled to 0°–5° C. in an ice-water bath. The solution was stirred at 0°–5° C. for 2 h and was then poured into cold 1N HCl solution (150 mL). The THF layer was separated and the aqueous (aq.) layer was extracted with EtOAc (100 mL). Organic extracts were combined, dried (MgSO₄), filtered and concentrated. The crude oil was chromatographed on a silica gel column and eluted with 5–20% ethylacetate (EtOAc) in hexanes to obtain title 4-phenyl-but-1-ene-3-one (7.62 g, 73%) as an oil.

C.

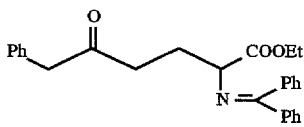

A 40% (w/w) solution of Triton-B in methanol (200 μL) was added dropwise to a stirred solution of Part A glycinate (15.35 g, 57.5 mmol) and Part B ketone (7.62 g, 52.2 mmol) in distilled THF (150 mL), cooled to 0°–5° C. After 1 h, the solution was diluted with water (75 mL). The THF layer was separated and the aq. layer was extracted with EtOAc (50 mL). Organic extracts were combined, dried (MgSO4), filtered and concentrated. The crude oil was chromatographed on a silica gel column and eluted with 10–30% EtOAc in hexanes to obtain title compound (8.37 g, 71%) as an oil.

D.

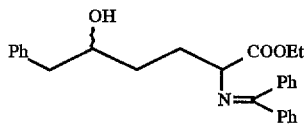

A solution of sodium borohydride (770 mg, 20.26 mmol) in water (10 mL) was added dropwise to a stirred solution of Part C ester (8.37 g, 20.26 mmol) in distilled THF (100 mL), cooled to 0°–5° C. After 1 h, the solution was poured into satd. NH₄Cl solution (100 mL). The THF layer was separated and the aq. layer was extracted with EtOAc (50 mL). Organic extracts were combined, dried (MgSO₄), filtered and concentrated. The crude oil was chromatographed on a silica gel column and eluted with 10–30% EtOAc in hexanes to obtain title compound (7.83 g, 93%, mixture of epimers) as an oil.

E.

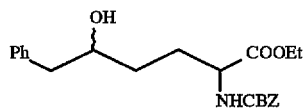

A 1N aq. solution of hydrochloric acid (25 mL) was added to a vigorously stirred solution of Part D ester (7.83 g, 18.87 mmol) in ether (75 mL). After 2 h, the mixture was cooled to 0°–5° C. in an ice-water bath and solid K₂CO₃ (8.28 g, 60 mmol) was added. Benzylchloroformate (5.12 g, 30 mmol) was added dropwise over a period of 5 min. After 1 h, the mixture was diluted with water (50 mL). The ether layer was separated and the aq. layer was extracted with EtOAc (50 mL). Organic extracts were combined, dried (MgSO₄), filtered and concentrated. The crude oil was chromatographed on a silica gel column and eluted with 20–50% EtOAc in hexanes to obtain title compound (6.88 g, 95%, mixture of epimers) as an oil.

F.

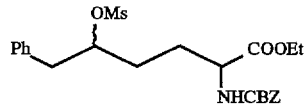

Methanesulfonyl chloride (2.29 g, 20 mmol) was added dropwise to a stirred solution of Part E ester (6.88 g, 17.87 mmol) in dichloromethane (40 mL) and triethyl amine (4.2 mL, 30 mmol) at 0°–5° C. After 1 h, the mixture was diluted with dichloromethane (60 mL) and water (50 mL). The dichloromethane extract was separated, dried (MgSO₄), filtered and concentrated. The crude oil was chromatographed on a silica gel column and eluted with 25–50% EtOAc in hexanes to obtain title compound (8.04 g, 97%, mixture of epimers) as an oil.

G.

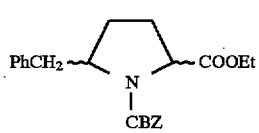

A solution of Part F ester (8.04 g, 17.37 mmol) in dry THF (15 mL) was added dropwise to a stirred suspension of sodium hydride (840 mg, 35 mmol, 60% in oil dispersion which was prewashed with ether) in THF (70 mL), cooled to 0°–5° C. in an ice-water bath. The mixture was stirred at 0°–5° C. for 30 min and then at RT overnight. Excess NaH was destroyed by addition of 1N HCl solution (50 mL). The THF layer was separated and the aq. layer was extracted with EtOAc (50 mL). Organic extracts were combined, dried (MgSO₄), filtered and concentrated. The crude oil was dissolved in ethanol (30 mL) and acetyl chloride (2.5 mL) was added. The solution was stirred at RT overnite, concentrated and the residue was chromatographed on a silica gel column. Elution with 20–40% EtOAc in hexanes afforded title racemic Z-5-benzyl-proline ethyl ester (5.51 g, 87%, 1:1 mixture of cis and trans-epimers) as a colorless oil.

H.

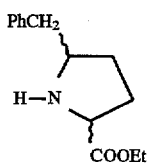

Palladium hydroxide (1.1 g, Pearlman's catalyst) was added to a stirred solution of Part G ester (5.51 g, 15.01 mmol) in 95% ethanol (100 mL). The reaction flask was equipped with a hydrogen filled balloon via a three-way stopcock. Air inside the flask was evacuated under reduced pressure and was then filled with hydrogen from the balloon. This operation was repeated (3×). Hydrogenolysis was continued overnite. The balloon was removed and the mixture was filtered through a pad of $MgSO_4$. Residual solid was washed with EtOAc (5 mL, 5×) and the filtrate was concentrated under reduced pressure and in vacuo to obtain title racemic 5-benzyl-proline ethyl ester (3.37 g, 96%, mixture of cis and trans epimers) as an oil.

I.

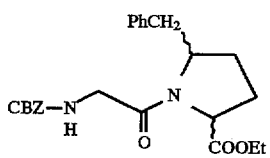

4-Methyl morpholine (2.2 mL, 20 mmol) was added dropwise to a stirred solution of Part H ester (2.33 g, 10 mmol), N-CBZ-glycine (2.09 g, 10 mmol) and N-hydroxybenztriazole (1.69 g, 12.5 mmol) in dimethylformamide (DMF) (50 mL). Water soluble carbodiimide (2 g, 10 mmol) was added and the solution was stirred at RT overnite. The mixture was diluted with EtOAc (100 mL) and washed with saturated (satd.) $KHSO_4$ solution (35 mL, 2×), satd. $NaHCO_3$ solution (50 mL, 2×) and 10% aq. LiCl solution (20 mL, 3×), dried (MgSO4), filtered and concentrated. The crude oil was chromatographed on a silica gel column and eluted with 25–75% EtOAc in hexanes to obtain title compound (3.35 g, 78%) as an oil.

J.

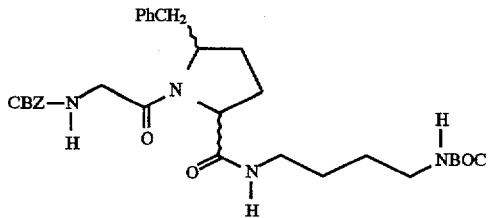

A 1N solution of sodium hydroxide in water (16 mL, 16 mmol) was added to a stirred solution of Part I ester (3.35 g, 7.9 mmol) in methanol (50 mL). The solution was stirred at RT overnight, acidified with 1N HCl solution (30 mL) and extracted with EtOAc (75 mL, 2×). EtOAc extracts were combined, washed with brine (50 mL), dried ($MgSO_4$), filtered and concentrated to obtain crude acid (3.11 g, 100%) as a foam.

4-Methyl morpholine (880 µL, 8 mmol) was added dropwise to a stirred solution of crude acid (1.5 g, 3.79 mmol), mono-N-BOC-butane 1,4-diamine (940 mg, 5 mmol) and 1hydroxybenzotriazole (775 mg, 5 mmol) in DMF (20 mL). Water soluble carbodiimide (1 g, 5 mmol) was added and the solution was stirred at RT overnight. The mixture was diluted with EtOAc (100 mL) and washed with satd. $KHSO_4$ solution (30 mL), satd. $NaHCO_3$ solution (30 mL, 2×) and 10% aq. LiCl solution (15 mL, 3×), dried ($MgSO_4$), filtered and concentrated. The crude foam was chromatographed on a silica gel column and eluted with 30–75% EtOAc in hexanes, followed by EtOAc to obtain title compound (1.73 g, 81%) as a foam.

K.

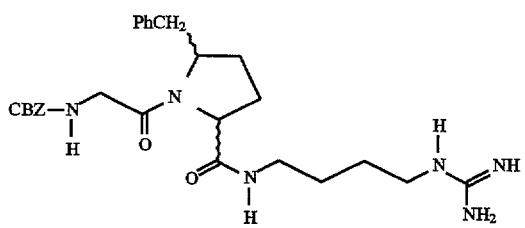

Part J compound (1.67 g, 2.95 mmol) was treated with trifluoroacetic acid (TFA) (20 mL) and stirred at room temperature for three hours. The TFA was removed in vacuo and toluene was added three times and removed in vacuo. The residue was dissolved in ethanol (50 mL), to which amidinesulfonic acid (512 mg, 4.13 mmol) and triethylamine (1.5 mL) were added. The mixture was stirred overnight at room temperature and then concentrated to dryness in vacuo. The crude material was purified by preparative HPLC. Fractions containing clean title compound were combined and lyophilized to provide title compound as a white solid (1.433 g, 74%).

Analysis: Calcd for $1.1TFA+1.30 H_2O$: C, 53.34; H, 6.09; N, 12.78; F, 9.54.

Found: C, 53.34; H, 6.20, N, 12.65; F, 9.27.

EXAMPLE 2

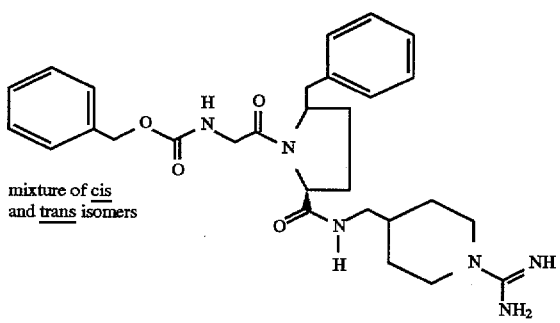

mixture of cis and trans isomers

A.

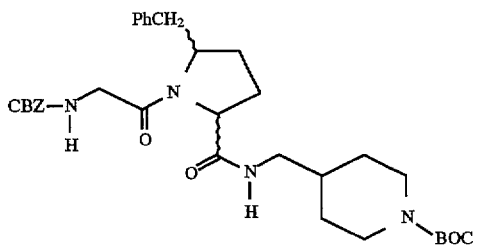

4-Methyl morpholine (880 μL, 8 mmol) was added dropwise to a stirred solution of crude acid prepared as described in Example 1 Part J (1.58 g, 4 mmol), N-BOC-4-aminomethyl-piperidine (1.0 g, 4.7 mmol) and 1-hydroxybenzotriazole (775 mg, 5 mmol) in DMF (25 mL). Water soluble carbodiimide (1.0 g, 5 mmol) was added and the solution was stirred at RT overnight. The mixture was diluted with EtOAc (125 mL) and washed with satd. KHSO$_4$ solution (40 mL), satd. NaHCO$_3$ solution (35 mL, 2×) and 10% aq. LiCl solution (25 mL, 2×), dried (MgSO4), filtered and concentrated. The crude oil was chromatographed on a silica gel column and eluted with 50–70% EtOAc in hexanes, followed by EtOAc to obtain title compound (1.71 g, 72%) as a white solid.

B.

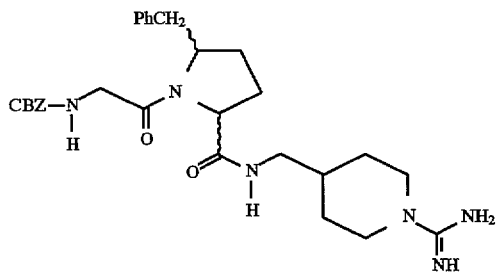

The Part A BOC compound (1.67 g, 2.82 mmol) was treated with TFA (20 mL) and stirred at room temperature for four hours. The TFA was removed in vacuo and toluene was added three times and removed in vacuo. The amine salt was dissolved in dimethylformamide (5 mL). H-pyrazole-1-carboxamidine (540 mg, 3.67 mmol) and diisopropylethyl amine (1.52 mL) were added. The mixture was stirred 20 hours at room temperature. TLC indicated that some starting material remained and the mixture was treated with additional H-pyrazole-1-carboxamidine (150 mg) and diisopropylethyl amine (0.5 mL) and stirred at room temperature an additional 16 hours. Ether (25 mL) was then added. Gummy material precipitated. The ether was decanted and the precipitate was washed with more ether. The gummy material was dissolved in methanol and taken to dryness in vacuo. The remaining material was purified by preparative HPLC. Fractions containing clean title compound were combined and lyophilized to provide a white solid (1.15 g, 57%).

Analysis: Calcd for 1.40 TFA+1.0 H$_2$O: C, 53.62; H, 5.86; N, 11.80; F, 11.20.

Found: C, 53.55; H, 5.57;, N, 11.56; F, 11.05.

EXAMPLE 3

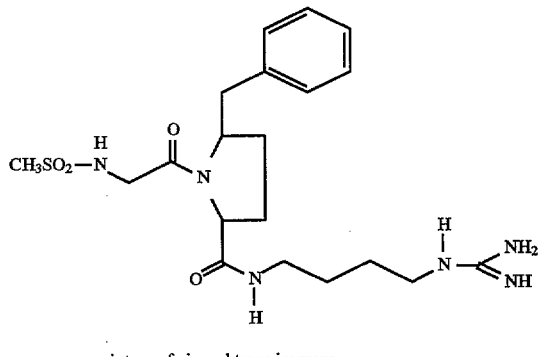

mixture of cis and trans isomers

A.

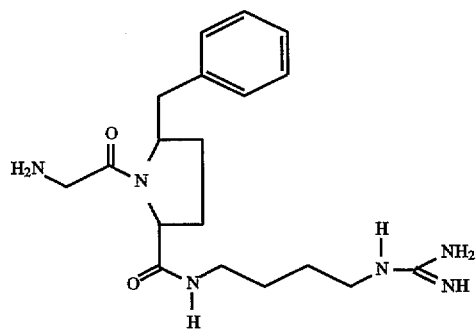

Example 1 compound (1.16 g, 1.765 mmol) was dissolved in methanol (MeOH) (60 mL) and treated with Pearlman's catalyst (300 mg). The flask was connected to a hydrogen filled balloon via a three way stopcock. Air inside the flask was removed and replaced with hydrogen from the balloon. This process was repeated three times. The mixture was stirred at room temperature 4.5 hrs. The catalyst was removed by filtration and the solvent was removed in vacuo to give crude title compound as a glass (962 mg, Quant). HPLC indicated that this was about 75% pure and it was used without purification.

B.

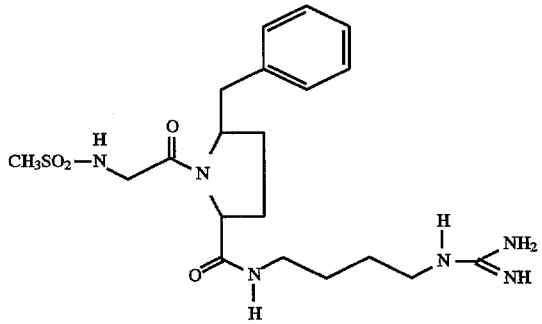

mixture of cis and trans isomers

Part A compound (750 mg, 1.537 mmol) was dissolved in a mixture of dichloromethane (12 mL) and distilled THF (24 mL). The solution was treated with triethylamine (860 µL) followed by dropwise addition of methanesulfonyl chloride (780 µL, 1.84 mmol). The mixture was stirred at room temperature for 5 hours and then treated with water (~2.5 mL). The mixture was taken to dryness in vacuo. The crude material was purified by preparative HPLC. Fractions containing title compound were combined and lyophilized to provide a white solid which was used to take NMR spectra. The material was recovered, dissolved in water (20 mL), passed through a millipore membrane and lyophilized to provide title compound as a white solid (339 mg, 36%).

Analysis calcd for 1.35 TFA+0.40 H$_2$O: C, 44.03; H, 5.61; N, 13.69; F, 12.54; S, 5.22.

Found: C, 44.42 H, 5.90;, N, 13.67; F, 12.52; S, 5.38.

EXAMPLE 4

Isomer A

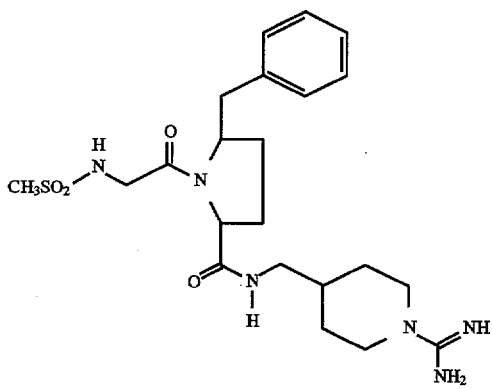

A. and B.

Isomer A and Isomer B

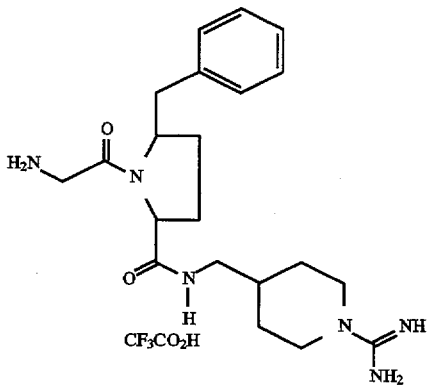

Example 2 compound (920 mg, 1.29 mmol) was dissolved in MeOH (60 mL) and treated with Pearlman's catalyst (300 mg). The flask was connected to a hydrogen filled balloon via a three way stopcock. Air inside the flask was removed and replaced with hydrogen from the balloon. This process was repeated three times. The mixture was stirred at room temperature 5 hrs. The catalyst was removed by filtration and the solvent was removed in vacuo to give a mixture of title Isomers A and B as a glass (720 mg, 97%). HPLC indicated that this was a mixture of isomers. The crude material was purified by preparative HPLC. Fractions containing title Isomer A were combined and lyophilized to provide a white solid (370 mg, ~50%). Fractions containing mainly title Isomer B were combined and lyophilized to provide a white solid (170 mg, ~23%).

C.

Isomer A

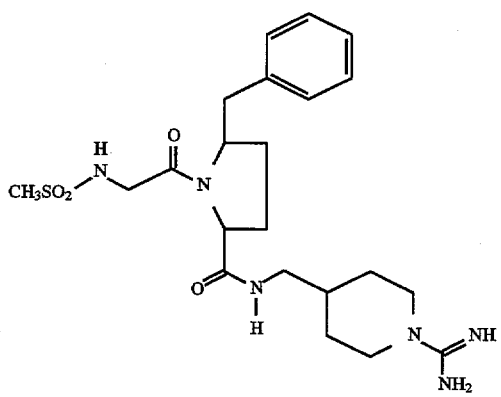

Part A Isomer A (370 mg, ~0.59 mmol was dissolved in distilled THF (12 mL). The solution was treated with triethylamine (730 µL) and cooled in an ice bath. Methanesulfonyl chloride (390 µL, 0.92 mmol) was added dropwise. The mixture was stirred at room temperature for 3 hours and then treated with water (~1 mL). The mixture was taken to dryness in vacuo. The crude material was purified by preparative HPLC. Fractions containing title compound were combined and lyophilized to provide a white solid which was used to take NMR spectra. The material was recovered, dissolved in water (30 mL), passed through a millipore membrane and lyophilized to provide title compound as a white solid (191 mg, 51%).

Analysis calcd for 1.2 TFA+1.20 H$_2$O: C, 46.00; H, 5.95; N, 13.19; F, 10.74; S, 5.03.

Found: C, 46.05 H, 5.96;, N, 12.84; F, 10.45; S, 5.23.

EXAMPLE 5

Isomer B

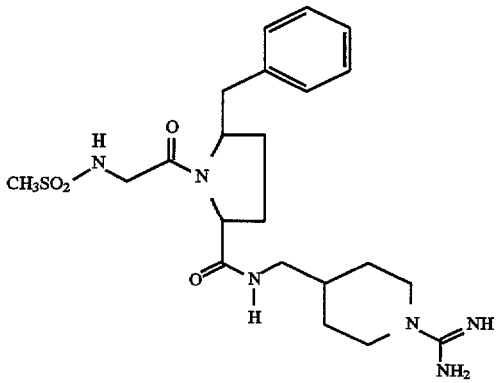

Example 4 Part B (Isomer B) compound (170 mg, ~0.22 mmol, containing about 5% of Isomer A by HPLC) was dissolved in distilled THF (6 mL). The solution was treated with triethylamine (365 µL) and cooled in a wet ice bath. Methanesulfonyl chloride (195 µL, 0.46 mmol) was added dropwise. The mixture was stirred at room temperature for 3 hours and then treated with water (~1 mL). The mixture was taken to dryness in vacuo. The crude material was purified by preparative HPLC. Fractions containing title compound were combined and lyophilized to provide a white solid which was used to take NMR spectra. The material was recovered, dissolved in water (15 mL), passed through a millipore membrane and lyophilized to provide title compound as a white solid (99 mg, 70%).

Analysis calcd for 1.2 TFA+1.40 $H_2O$: C, 45.74; H, 5.98; N, 13.12; F, 10.68; S, 5.00.

Found: C, 45.70 H, 5.86;, N, 12.92; F, 10.75; S, 5.15.

Following the procedures of Example 1 to 5, the following examples of compounds of the invention may be prepared.

TABLE I
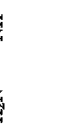
| Example No. | R⁴ | Z | R | R¹ | R² | R³ | n | p | Q | A | R⁶ |
|---|---|---|---|---|---|---|---|---|---|---|---|
| 6 | $CH_3$ | NH | $CH_2OH(S)$ | $CH_3$ | H | $CH_3$ | 1 | 0 | — | 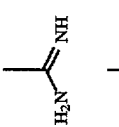 | 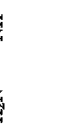 |
| 7 | H | O | H | $CH_2CH_2C_6H_5$ | OH | H | 0 | 1 | CO | 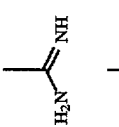 | 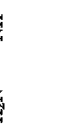 |
| 8 | $CH_3SO_2$ | $NCH_2C_6H_5$ | $-CH_2C_6H_5(R)$ | $CH_2C_6H_5$ | $OCH_3$ | $CH_3$ | 0 | 2 | — | 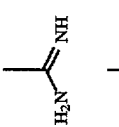 | 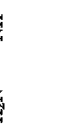 |
| 9 | 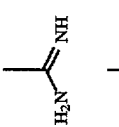 | $NCH_3$ | $-CH_2C_6H_5(S)$ | $CH_3$ | H | $CH_3$ | 1 | 0 | — |  | 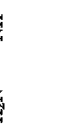 |

TABLE I-continued $$R^4-Z-\overset{\overset{O}{\|}}{\underset{\underset{H}{|}}{C}}-\overset{R^1}{\underset{}{C}}H-\overset{R^2}{\underset{}{C}}H-\overset{R^3}{\underset{}{C}}H_2-\overset{(CH_2)_n}{\underset{}{C}}H-\overset{O}{\underset{}{C}}-NH-(CH_2)_p-Q-A-R^6$$

| Example No. | R⁴ | Z | R | R¹ | R² | R³ | n | p | Q | A | R⁶ |
|---|---|---|---|---|---|---|---|---|---|---|---|
| 10 | H | O | —CH₂CH₂CONH₂(S) | CH₂C₆H₅ | H | H | 1 | 0 | — | phenyl (1,4) | —CH₂NH₂ |
| 11 | C₆H₅ | NH | —CH₂CH₂CONH₂(R) | CH₃ | H | CH₃ | 1 | 1 | CO | cyclohexyl (1,4) | —CH₂NH₂ |
| 12 | 4-pyridyl | NC₆H₅ | —CH(OH)CH₃(S—Thr) | C₆H₅ | —CHCH₂CH₂CH— | | 0 | 1 | — | pyridyl (1,4) | —NH—C(=NH)NH₂ |
| 13 | 3-methylisoxazol-5-yl | NH | CH(OH)CH₃(S-alloThr) | CH₂-cyclohexyl | CH₃ | H | 1 | 2 | CO | N-methylpyrrolidinone | C(=NH)NH₂ |
| 14 | 2-methylthiazol-4-yl | O | 3-ethylindol-... (R) | C₂H₅ | SCH₃ | CH₃ | 1 | 1 | — | N-methylpiperidinyl | C(=NH)NH₂ |

TABLE I-continued
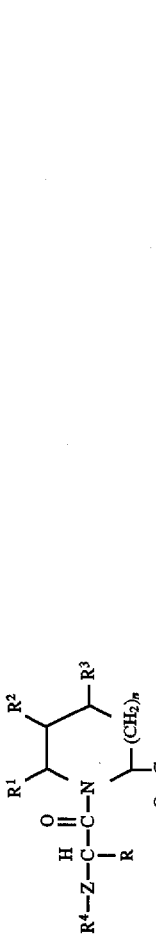
| Example No. | R⁴ | Z | R | R¹ | R² | R³ | n | p | Q | A | R⁶ |
|---|---|---|---|---|---|---|---|---|---|---|---|
| 15 | quinoline-8-SO₂— | NH | —CH₂CH₂CO₂H(R) | CH₂C₆H₅ | H | CH₃ | 0 | 0 | CO | 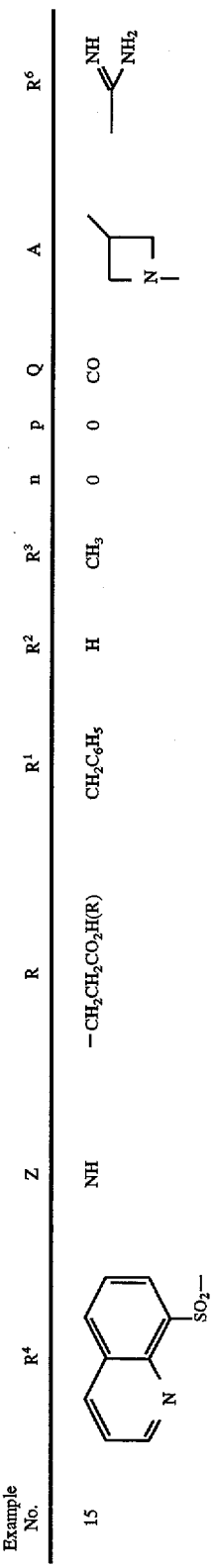 | =NH, NH₂ |
| 16 | H | O | CH₂OCH₂Ph(R) | CH₃ | H | H | 1 | 0 | — |  | =NH, NH₂ |
| 17 | C₆H₅CH₂ | NCH₃ | CH₂CH₂Ph(S) | CH₂C₆H₅ | H | H | 1 | 1 | — | 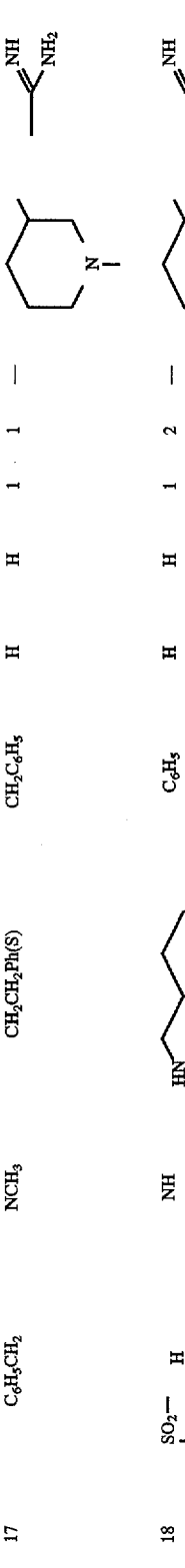 | =NH, NH₂ |
| 18 | 2-methyl-tetrahydroquinoline-8-SO₂— | NH | 4-(N-methylpiperidinyl)methyl-NH | C₆H₅ | H | H | 1 | 2 | — |  | =NH, NH₂ |

TABLE II

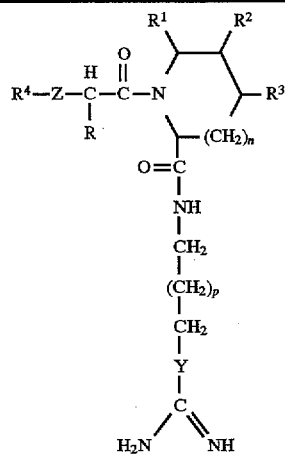

| Example No. | R⁴ | Z | R | R¹ | R² | R³ | n | m | Y |
|---|---|---|---|---|---|---|---|---|---|
| 19 | CH₃SO₂ | NH | CH₂OH(S) | CH₂–⟨cyclohexyl⟩ | H | CH₃ | 1 | 0 | NH |
| 20 | H | O | H | C₂H₄C₆H₅ | OH | H | 0 | 1 | S |
| 21 | ⟨2-pyridyl⟩ | NCH₂C₆H₅ | –CH₂C₆H₅(R) | CH₃ | OCH₃ | CH₃ | 0 | 2 | NH |

What is claimed is:

1. A compound having the structure

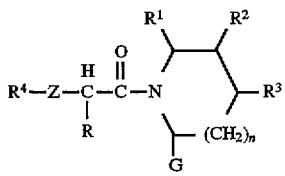

including all stereoisomers, wherein n is 0, 1 or 2;

Z is NR⁷ or O, where R⁷ is H, lower alkyl, aryl or arylalkyl;

G is an amido moiety which includes a cyclic member which is free of

a group in the ring;

R is hydrogen, hydroxyalkyl, hydroxyalkyl(alkyl), aminoalkyl, lower alkyl, cycloalkyl, arylalkyl, alkenyl, alkynyl, amidoalkyl, arylalkoxyalkyl or an amino acid side chain, either protected or unprotected;

R¹ is lower alkyl exclusive of methyl, cycloalkyl, aryl, or arylalkyl; or R¹ and R² together with the carbons to which they are attached form a cycloalkyl, aryl or heteroaryl ring;

R² and R³ are independently hydrogen, lower alkyl, cycloalkyl, aryl, arylalkyl, hydroxy, alkoxy, oxo, thioketal, thioalkyl, thioaryl, amino or alkylamino; or R² and R³ together with the carbons to which they are attached form a cycloalkyl, aryl or heteroaryl ring;

R⁴ is H, lower alkyl, arylalkyl, aryl,

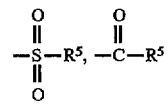

or —CO₂R⁵, where R⁵ is lower alkyl, aryl, arylalkyl, cycloheteroalkyl, heteroaryl, quinolinyl or tetrahydroquinolinyl;

including pharmaceutically acceptable salts thereof.

2. The compound as defined in claim 1 wherein G is

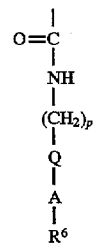

wherein p is 0, 1 or 2;

Q is a single bond or $$\begin{array}{c} | \\ C=O; \\ | \end{array}$$

A-R⁶ is an azacycloalkyl ring of 4 to 8 carbons in the ring or an azaheteroalkyl ring of 4 to 8 carbons in the ring of the structure $$\begin{array}{c} X \\ \diagdown \\ (CH_2)_q \\ \diagup \\ Y^1 \diagdown Y^2 \quad N \\ | \\ R^6 \end{array}$$

where X is CH₂, O, S or NH;

q is 0, 1, 2, 3 or 4, provided that q is 0, 1, 2, 3 or 4 if X is CH₂;

q is 2, 3 or 4 if X is O, S or NH;

Y¹ and Y² are independently H, lower alkyl, halo or keto;

R⁶ is amidino;

where A is azaheteroalkyl, then there must be at least a 2-carbon chain between X and any N atom in the ring or outside the ring.

3. The compound as defined in claim 2 wherein Q is a single bond.

4. The compound as defined in claim 2 wherein A-R⁶ is $$\begin{array}{c} X \\ \diagdown \\ (CH_2)_q \\ \diagup \\ Y^1 \diagdown Y^2 \quad N \\ | \\ R^6 \end{array}$$

5. The compound as defined in claim 4 wherein X is CH₂ or NH, and Y¹ and Y² are each H.

6. The compound as defined in claim 4 wherein G is $$\begin{array}{c} | \\ O=C \\ | \\ NH \\ | \\ (CH_2)_p \\ \diagup \diagdown \\ \quad (CH_2)_q \\ \diagdown \diagup \\ N \\ H_2N \diagdown \diagup NH \end{array}$$

Z is NH;

R¹ is arylalkyl or lower alkyl exclusive of methyl;

R² and R³ are each H; R⁴ is lower alkyl, arylalkyloxycarbonyl, or alkylsulfonyl; n is 0 or 1; and R is hydrogen.

7. The compound as defined in claim 6 having the structure

[structure diagram of compound with R⁴—N—C(H)—C(=O)—N group, phenyl CH₂ branch, C=O—NH—CH₂-piperidine with amidino]

where R⁴ is $$\begin{array}{c} O \\ \| \\ C_6H_5CH_2OC-, \end{array}$$

CH₃SO₂— or CH₃CH₂—.

8. The compound as defined in claim 2 wherein R⁴ is arylalkyloxycarbonyl or alkylsulfonyl, R² and R³ are each H, R¹ is arylalkyl or lower alkyl exclusive of methyl and R is H.

9. The compound as defined in claim 2 having the structure

[two structural diagrams of compounds, one with benzyloxycarbonyl group and one with CH₃SO₂ group, each connected to benzyl-substituted pyrrolidine linked to piperidinyl-guanidine]

including stereoisomers thereof and pharmaceutically acceptable salts thereof.

10. A method of inhibiting or preventing formation of blood clots, which comprises administering to a patient in need of treatment a therapeutically effective amount of a compound as defined in claim 1.

11. A pharmaceutical composition comprising a compound as defined in claim 1 and a pharmaceutically acceptable carrier therefor.

* * * * *